US009255978B2

(12) United States Patent
Fallone et al.

(10) Patent No.: US 9,255,978 B2
(45) Date of Patent: Feb. 9, 2016

(54) MAGNETIC ASSEMBLY AND METHOD FOR DEFINING A MAGNETIC FIELD FOR AN IMAGING VOLUME

(71) Applicant: Alberta Health Services, Edmonton (CA)

(72) Inventors: B. Gino Fallone, Edmonton (CA); Tony Tadic, Edmonton (CA); Brad Murray, Sherwood Park (CA)

(73) Assignee: Alberta Health Services, Alberta (CA)

( * ) Notice: Subject to any disclaimer, the term of this patent is extended or adjusted under 35 U.S.C. 154(b) by 32 days.

(21) Appl. No.: 14/174,423

(22) Filed: Feb. 6, 2014

(65) Prior Publication Data

US 2014/0229141 A1    Aug. 14, 2014

Related U.S. Application Data

(63) Continuation of application No. 13/000,877, filed as application No. PCT/CA2009/000860 on Jun. 25, 2009, now abandoned.

(60) Provisional application No. 61/129,412, filed on Jun. 24, 2008.

(51) Int. Cl.
*G01R 33/54* (2006.01)
*G01R 33/38* (2006.01)
(Continued)

(52) U.S. Cl.
CPC ............ *G01R 33/543* (2013.01); *G01R 33/383* (2013.01); *G01R 33/3806* (2013.01);
(Continued)

(58) Field of Classification Search
CPC ...... H01F 7/0273; H01F 7/0278; G06F 17/50
USPC ................................ 335/284, 296–303, 306
See application file for complete search history.

(56) References Cited

U.S. PATENT DOCUMENTS 2,984,782 A    5/1961    Dicke
3,919,678 A    11/1975   Penfold
(Continued)

FOREIGN PATENT DOCUMENTS

EP    0 262 880 A2    4/1988
EP    0 691 526 A1    1/1996
(Continued)

OTHER PUBLICATIONS

Office Action for Japanese Application No. 2011-515033 dated Sep. 16, 2014.
(Continued)

*Primary Examiner* — Mohamad Musleh
(74) *Attorney, Agent, or Firm* — Alston & Bird LLP

(57) ABSTRACT

Disclosed herein is a magnet assembly that includes at least two magnets arranged in a fixed spaced relationship with one another thereby to define a space between the magnets that encompasses an imaging volume. Each of the magnets produces a variety of magnetic field strengths across inward-facing surfaces thereof that, in combination, produce an acceptably homogeneous magnetic field in the imaging volume. Also disclosed is a method of defining a magnetic field for an imaging volume. The method comprises generating an initial model of a magnet assembly; estimating a magnetic field for the imaging volume based on the model; calculating deviation between the estimated magnetic field and a target magnetic field for the imaging volume; and updating the model to reduce the deviation by modifying the magnet assembly to produce a variety of magnetic field strengths that, in combination, produce substantially the target magnetic field in the imaging volume.

14 Claims, 8 Drawing Sheets

(51) Int. Cl.

| | | |
|---|---|---|
| *G01R 33/383* | (2006.01) | |
| *G21K 1/093* | (2006.01) | |
| *G06F 17/50* | (2006.01) | |
| *A61B 5/055* | (2006.01) | |
| *A61N 5/10* | (2006.01) | |
| *H01F 7/02* | (2006.01) | |

(52) U.S. Cl.
CPC .............. *G06F17/50* (2013.01); *G21K 1/093* (2013.01); *A61B 5/055* (2013.01); *A61N 5/1043* (2013.01); *A61N 2005/1087* (2013.01); *A61N 2005/1089* (2013.01); *H01F 7/0278* (2013.01)

(56) References Cited

U.S. PATENT DOCUMENTS

| | | | |
|---|---|---|---|
| 3,924,211 A | | 12/1975 | Ioffe et al. |
| 4,310,819 A | * | 1/1982 | Morita et al. ................. 335/212 |
| 4,445,102 A | | 4/1984 | Thorn et al. |
| 4,506,240 A | | 3/1985 | Shores et al. |
| 4,672,346 A | | 6/1987 | Miyamoto et al. |
| 4,679,022 A | | 7/1987 | Miyamoto et al. |
| 4,766,378 A | | 8/1988 | Danby et al. |
| 4,870,380 A | | 9/1989 | McGinley |
| 4,943,774 A | | 7/1990 | Breneman et al. |
| 5,323,135 A | | 6/1994 | Schmidt et al. |
| 5,382,904 A | | 1/1995 | Pissanetzky |
| 5,382,905 A | | 1/1995 | Miyata et al. |
| 5,436,607 A | | 7/1995 | Chari et al. |
| 5,448,213 A | | 9/1995 | Kalsi |
| 5,539,366 A | | 7/1996 | Dorri et al. |
| 5,684,399 A | | 11/1997 | Bayer |
| 6,011,396 A | | 1/2000 | Eckels et al. |
| 6,020,805 A | | 2/2000 | Børja |
| 6,150,819 A | * | 11/2000 | Laskaris et al. ................ 324/319 |
| 6,150,911 A | * | 11/2000 | Katznelson et al. .......... 335/299 |
| 6,198,286 B1 | | 3/2001 | Trequattrini et al. |
| 6,335,670 B1 | | 1/2002 | Kinanen |
| 6,340,888 B1 | | 1/2002 | Aoki et al. |
| 6,535,092 B1 | | 3/2003 | Hurley et al. |
| 6,570,475 B1 | | 5/2003 | Lvovsky et al. |
| 6,642,826 B1 | | 11/2003 | Aoki et al. |
| 6,707,363 B1 | | 3/2004 | Abele |
| 6,897,751 B2 | | 5/2005 | Aoki et al. |
| 7,071,694 B1 | | 7/2006 | Kruip |
| 7,143,507 B2 | | 12/2006 | Aoki et al. |
| 7,463,129 B1 | | 12/2008 | Danby et al. |
| 7,479,859 B2 | | 1/2009 | Gerbert |
| 7,667,462 B2 | | 2/2010 | Song et al. |
| 7,706,858 B1 | | 4/2010 | Green et al. |
| 7,796,002 B2 | | 9/2010 | Hashimoto et al. |
| 7,928,730 B2 | | 4/2011 | Aoki et al. |
| 2002/0097122 A1 | | 7/2002 | Rapoport |
| 2003/0011455 A1 | | 1/2003 | Wakuda et al. |
| 2003/0011456 A1 | | 1/2003 | Yoshida et al. |
| 2003/0048163 A1 | | 3/2003 | Watanabe et al. |
| 2005/0052266 A1 | | 3/2005 | Doi |
| 2005/0068138 A1 | | 3/2005 | Amm et al. |
| 2005/0280487 A1 | * | 12/2005 | Huang et al. .................. 335/296 |
| 2009/0231073 A1 | | 9/2009 | Horisaka et al. |

FOREIGN PATENT DOCUMENTS

| | | |
|---|---|---|
| EP | 0 982 598 A2 | 3/2000 |
| GB | 2 276 945 A | 10/1994 |
| GB | 2 425 842 A | 11/2006 |
| JP | 3-273603 A | 12/1991 |
| JP | 2002-336215 A | 11/2002 |
| JP | 2003-024299 A | 1/2003 |
| JP | 2003-265434 A | 9/2003 |
| JP | 2004-236747 A | 8/2004 |
| JP | 2005-118098 A | 5/2005 |
| JP | 2007-037835 A | 2/2007 |
| WO | WO-2007/045075 A1 | 4/2007 |
| WO | WO-2007/045076 A1 | 4/2007 |

OTHER PUBLICATIONS

International Preliminary Report on Patentability/Written Opinion for Application No. PCT/CA2009/000860 dated Jan. 5, 2011.
Office Action for European Application No. 12 17 5576.3 dated Jul. 22, 2014.
Office Action for European Application No. EP 12 17 5576 dated Aug. 14, 2012.
Marble, A. E. et al., *Designing Static Fields for Unilateral Magnetic Resonance by a Scalar Potential Approach*, IEEE Transactions on Magnetics, vol. 43, No. 5 (May 2007) 1903-1911 (XP011177275).
Morgan, P. N. et al., *Resistive Homogeneous MRI Magnet Design by Matrix Subset Selection*, Magnetic Resonance in Medicine, vol. 41 (Jan. 1999) 1221-1229 (XP002573904).
Tadic, T. et al., *Three-Dimensional Nonaxisymmetric Pole Piece Shape Optimization for Biplanar Permanent-Magnet MRI Systems*, IEEE Transactions on Magnetics, vol. 47, No. 1 (Jan. 2011) 231-238 (XP011340809).
Office Action for Canadian Application No. 2,728,108 dated Jan. 14, 2014.
Office Action for Japanese Application No. 2011-515033 dated Oct. 15, 2013.
International Search Report for Application No. PCT/CA2009/000860 dated Oct. 2, 2009.
Supplementary European Search Report for European Patent Application No. 09 76 8661, completed Nov. 30, 2011.
Office Action for Chinese Application No. 200980124177.X dated Sep. 5, 2012.
Ryu, J.S., et al.; "3-D Optimal Shape Design of Pole Piece in Permanent Magnet MRI Using Parameterized Nonliner Design Sensitivity Analysis"; IEEE Transactions on Magnetics; vol. 42; No. 4; Apr. 2006; pp. 1351-1354.
Office Action from corresponding Canadian Patent Application No. 2,728,108, dated Feb. 18, 2015.
Extended European Search Report from corresponding European Patent Application No. 09768661.2 dated Dec. 13, 2011.

* cited by examiner

MAGNETIC ASSEMBLY AND METHOD FOR DEFINING A MAGNETIC FIELD FOR AN IMAGING VOLUME

CROSS-REFERENCE TO RELATED APPLICATIONS

This application is a continuation of U.S. application Ser. No. 13/000,877, filed Mar. 25, 2011, which is a national phase entry of PCT/CA2009/000860 filed Jun. 25, 2009, which claims priority to U.S Provisional Patent Application No. 61/129,412, filed Jun. 24, 2008, the entire contents of which are incorporated herein by reference.

FIELD OF THE INVENTION

The present invention relates generally to magnetic fields with predetermined specially desired characteristics, and more particularly to magnetic assembly and method for defining a magnetic field for an imaging volume.

BACKGROUND OF THE INVENTION

Magnetic Resonance Imaging, or MRI, is a well-known imaging technique during which an object, such as a human patient, is placed into an MRI machine and subjected to a uniform magnetic field produced by a polarizing magnet housed within the MRI machine. Radio frequency (RF) pulses, generated by an RF coil housed within the MRI machine, are used to scan target tissue of the patient. MRI signals are radiated by excited nuclei in the target tissue in the intervals between consecutive RF pulses and are sensed by the RF coil. During MRI signal sensing, finely controlled magnetic field gradients are switched rapidly to alter the uniform magnetic field at localized areas thereby to allow spatial localization of MRI signals radiated by selected slices of the target tissue. The sensed MRI signals are in turn digitized and processed to reconstruct images of the target tissue slices using one of many known techniques.

In a system capable of performing MRI, a strong uniform static magnetic field is required in order to align the nuclear spins of the object within a particular imaging volume. This uniform static magnetic field is normally produced by a permanent or coil magnet assembly with a magnetic field strength on the order of 0.1 to 4.7 Tesla within the imaging volume. During sensing, the finely controlled magnetic field gradients imposed in the imaging volume allow for discrimination amongst nuclear spins at different locations. However, inhomogeneities in the static magnetic field within the imaging volume are inseparable from the magnetic field gradients during image acquisition and directly lead to geometric distortions in the resulting images. These distortions are especially detrimental when the MRI system is to be used in conjunction with another procedure that relies on the geometric accuracy of the acquired images, such as, but not limited to, radiation therapy. Consequently, significantly reducing static magnetic field inhomogeneities is extremely important in order to achieve images that are of a high quality and that have a high degree of geometric accuracy. For example, acceptable image quality can be achieved where the level of inhomogeneity is on the order of 10 ppm within the imaging volume.

It is known to reduce axisymmetric and non-axisymmetric static magnetic field inhomogeneities using techniques such as passive shimming. Passive shimming is performed after the magnetic assembly has been manufactured, and involves strategically placing additional pieces of magnetic material in and around the imaging volume. The additional pieces of magnetic material are typically of various shapes including rings, ring segments, cylinders, and prisms. While shimming has in some applications been effective in limiting inhomogeneity in the imaging volume, its effectiveness is limited by the extent to which the initial field inhomogeneities are present after manufacturing. As such, significant constraints are placed on the design of magnet assemblies, and by the requirement of maintaining a suitably large and accessible space within the magnet assembly for the object being examined.

Attempts to circumvent the limitations of passive shimming techniques have been made by improving the design of the manufactured magnet assemblies in order to reduce inherent axisymmetric field inhomogeneities. In the present state of the art for bi-planar magnets, the opposing surfaces of the magnet pole pieces are contoured in such a way that the pole pieces are shaped axisymmetrically about an axis generally extending towards the opposing pole piece surface. For example, the most common such pole piece design is known as a rose-ring design, in which the surface of the pole piece which is closest to the imaging volume is entirely flat with the exception of a ring of magnetic material placed along the periphery of the said pole piece surface. More particularly, a graph of axial distance of the pole piece surface along the axis, versus radial distance from the axis is a line of zero slope with a single vertical step at the radial position of the rose-ring.

One magnet assembly design disclosed in U.S. Pat. No. 5,539,366 consists of axisymmetrically shaped pole pieces for which a graph of axial distance, of the pole piece surface along the axis, versus radial distance from the axis is a piecewise linear curve, or is a non-linear curve having a continuous slope with at least two sign reversals. Both such designs are limited in that points on the surface regions of the pole pieces located an identical radial distance from the axis are also located a common axial distance along the axis, and thus only axisymmetric magnetic field inhomogeneities can be reduced prior to shimming. Furthermore, these systems are massive and immobile as the pole piece sizes are necessarily very large, and therefore are not suitable for movement relative to the subject being examined.

Often other objects and/or devices are placed in the vicinity of an MRI device. For example, described in PCT Patent Application Publication Number WO 2007/045076 A1 to Fallone et al., the contents of which are incorporated entirely herein by reference, is an integrated external beam radiotherapy and MRI system, wherein a linear accelerator (linac) is coupled to an MRI apparatus for providing simultaneous imaging and treatment. Unfortunately, current state of the art magnet assembly design does not address the effects of including objects or additional therapeutic or diagnostic devices within or proximate to the magnet assemblies, while providing acceptably homogeneous imaging volumes and/or other volumes with specific magnetic field properties, and ensuring that the size of the magnet assembly is manageable. The operation of such additional devices may be affected by the presence and/or characteristics of the magnetic field at their location and may themselves alter the characteristics of the magnetic field in the imaging volume. Furthermore, the incorporation of such objects or devices within or proximate the magnet assembly may require a particular volume of free space to be vacated from the magnet assembly, such as a large hole through the magnet structure, either for placement of the object or device, or for providing a benefit in performance of the object or device itself. For example, it may be advantageous to align the magnetic fields produced by a magnet assembly with the direction of electrons in a linac waveguide (or the protons produced by the linac for proton therapy) for image guided radiotherapy, particularly to reduce subsequent perturbations in patient radiation dosimetry. In general, such vacated volumes significantly affect the magnetic field produced by the magnet assembly and contribute to a highly inhomogeneous field in the imaging volume.

It is therefore an object of the invention to provide a magnet assembly and a method for defining a magnetic field for an imaging volume for that mitigates or obviates at least one of the above-described disadvantages of the prior art.

SUMMARY OF THE INVENTION

In accordance with an aspect, there is provided a magnet assembly comprising:

at least two magnets arranged in a fixed spaced relationship with one another thereby to define a space between the magnets that encompasses an imaging volume, each of the magnets producing a variety of magnetic field strengths across inward-facing surfaces thereof that, in combination, produce a substantially homogeneous magnetic field in the imaging volume.

The variety of magnetic fields across the inward-facing surfaces of the magnets enables production of a substantially homogenous magnetic field that is acceptable for imaging in an imaging volume, and that is of a sufficient size without necessarily resorting to use of very large magnets. As such, the production of a variety of magnetic fields across the inward-facing surfaces of the magnets provide a configuration that enables a more compact magnet assembly for a given imaging volume.

In accordance with another aspect, there is provided a Magnetic Resonance Imaging (MRI) device comprising:

the magnet assembly described above; and a detector detecting radiofrequency signals emitted by protons within the imaging volume when re-aligning with the substantially homogeneous magnetic field after perturbation, wherein imaging is based on the detected radiofrequency signals.

In accordance with another aspect, there is provided a method of defining a magnetic field for an imaging volume, the method comprising:

generating an initial model of a magnet assembly;

estimating a magnetic field for the imaging volume based on the model;

calculating deviation between the estimated magnetic field and a target magnetic field for the imaging volume; and updating the model to reduce the deviation by modifying the magnet assembly to produce a variety of magnetic field strengths that, in combination, produce substantially the target magnetic field.

In an embodiment, the target magnetic field is a magnetic field that is acceptably homogeneous, the initial model is based on parameters specifying the magnet assembly, and the modifying comprises modifying one or more parameters representing the surface geometry of one or both inward-facing surfaces of two magnets of the magnet assembly.

According to another aspect, there is provided a computer readable medium having a computer readable program thereon for defining a magnetic field for an imaging volume, the computer program comprising:

computer program code generating an initial model of a magnet assembly;

computer program code estimating a magnetic field for the imaging volume based on the model;

computer program code calculating deviation between the estimated magnetic field and a target magnetic field for the imaging volume; and computer program code updating the model to reduce the deviation by modifying the magnet assembly to produce a variety of magnetic field strengths that, in combination, produce substantially the target magnetic field in the imaging volume.

In accordance with another aspect, there is provided a magnet assembly comprising:

at least two magnets arranged in a fixed spaced relationship with one another thereby to define a space therebetween, each of the magnets producing a variety of magnetic field strengths across inward-facing surfaces thereof that, in combination, produce a target magnetic field in a target volume.

In accordance with still another aspect, there is provided a method of defining a magnetic field for a target volume, the method comprising:

generating an initial model of a magnet assembly;

estimating a magnetic field for the target volume based on the model;

calculating deviation between the estimated magnetic field and a target magnetic field for the target volume; and updating the model to reduce the deviation by modifying the magnet assembly to produce a variety of magnetic field strengths that, in combination, produce substantially the target magnetic field in the target volume.

In accordance with still another aspect, there is provided a computer readable medium embodying a computer program for defining a magnetic field for a target volume, the computer program comprising:

computer program code generating an initial model of a magnet assembly;

computer program code estimating a magnetic field for the target volume based on the model;

computer program code calculating deviation between the estimated magnetic field and a target magnetic field for the target volume; and computer program code updating the model to reduce the deviation by modifying the magnet assembly to produce a variety of magnetic field strengths that, in combination, produce substantially the target magnetic field in the target volume.

The method described herein can be applied to the computer-based design of magnetic assemblies for use in medical applications, particularly those involving Magnetic Resonance Imaging (MRI) where a bi-planar magnet configuration (e.g. Helmholtz type) is to be employed. Such bi-planar magnet assemblies include those with spaced-apart first and second pole pieces with generally opposing first and second pole faces, such as, but not limited to, C-shaped magnets, two column magnets, or four column magnets. In such applications, the method can be utilized to produce magnet assemblies which produce a substantially uniform magnetic field in a particular imaging volume by way of reduction of axisymmetric and/or non-axisymmetric field inhomogeneities. More generally, the method described herein may be employed to produce a magnetic field with specially desired characteristics in a particular region within or proximate the magnetic assembly where additional objects or devices may be located whose operation may be affected by the presence and/or characteristics of the magnetic field. Such objects or devices may be x-ray tubes, medical linear accelerator waveguides (linac), flat-panel imagers, nuclear medicine or ultrasound imagers, or other devices. Such devices may be placed at the ends of the open space between the two poles. The method described herein is also applicable to the definition of a magnetic field in an imaging volume for magnet assemblies that include an opening in one or both of the magnet poles either in the centre or at any location, for positioning of any device at that location. Such placement may be provided for design or operational advantage, such as reduction in size and/or reducing perturbations in patient dosimetry in a treatment system that is integrated with imaging system and/or producing a particular magnetic field. For example, one particular configuration would be the positioning of a linear accelerator (linac) at a location within the magnet structure where the direction of electrons in the waveguide or photons produced by them is parallel to the magnetic field produced by the magnet thus decreasing the subsequent perturbations in patient radiation dosimetry.

Another benefit of the method disclosed herein is that it is applicable to numerous uses. For example, while in many applications it is desirable that there be a substantially homogeneous magnetic field in an imaging volume, the magnetic field in the imaging volume may, in certain applications, be a desired though substantially nonhomogeneous magnetic field having a particularly desired gradient, for example. More generally, the invention may be employed for the defining of magnetic fields in volumes not intended for imaging. For example, it may be desired to define a magnetic field for a volume for directing/guiding/changing the path of an electron or proton beam such as is done currently with the use of bending magnets.

The magnet assembly and method described herein may be applied in systems that integrate external beam radiotherapy and MRI systems and even such systems configured for use in rotation mode, such as those described in PCT Patent Applications Publication Nos. WO 2007/045076 A1 and WO 2007/045075 A1 both to Fallone et al., the contents of each of which are incorporated herein by reference in their entirety.

BRIEF DESCRIPTION OF THE DRAWINGS

Embodiments will now be described more fully with reference to the accompanying drawings in which.

DETAILED DESCRIPTION OF THE EMBODIMENTS

Figure 1:
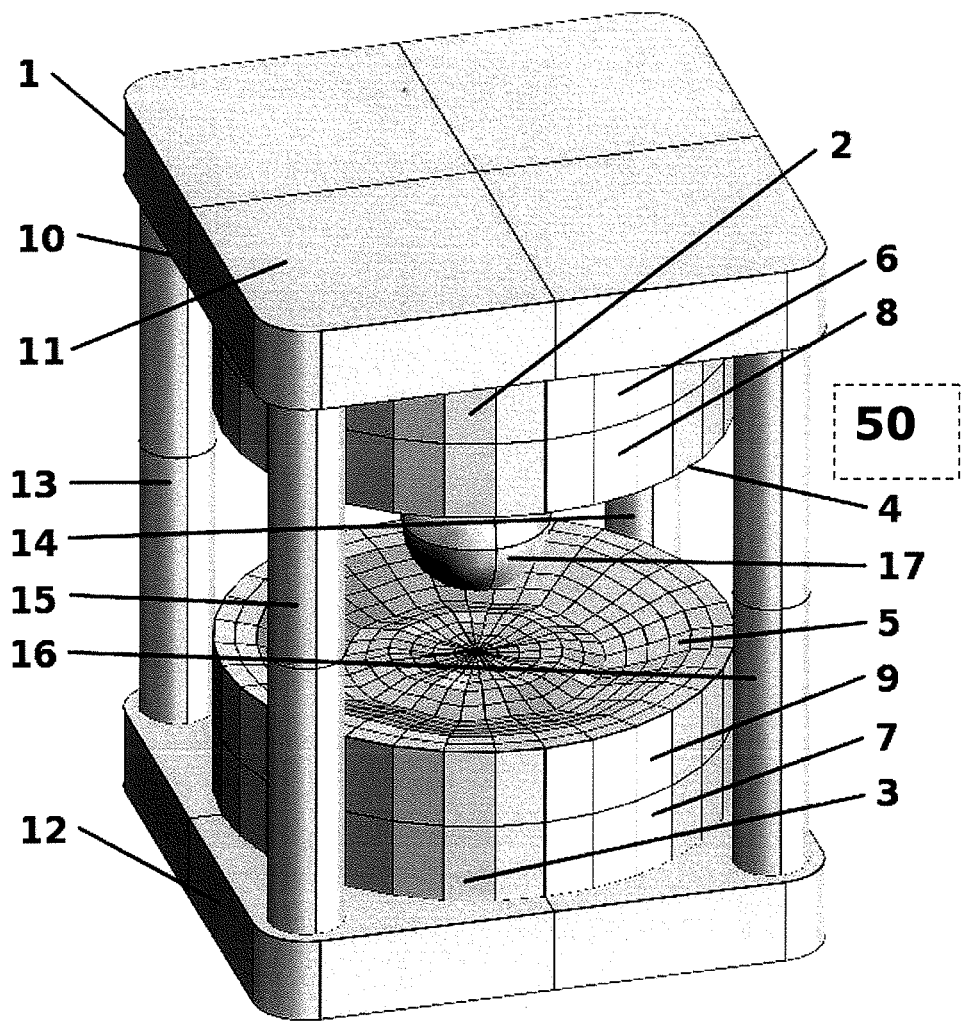
FIG. 1 is a perspective view of an open compact magnet assembly according to an embodiment.

Referring now to the drawings wherein like numerals indicate like elements throughout, FIGS. 1-4 show a magnet assembly 1 according to an embodiment. In this embodiment, magnet assembly 1 includes a first ferromagnetic pole assembly 2 and a second ferromagnetic pole assembly 3. The first and second ferromagnetic pole assemblies 2, 3 are arranged in a fixed, spaced relationship with one another as "biplanar" magnets thereby to define a space therebetween that encompasses an imaging volume 17 and is large enough to receive an object (not shown) to be imaged at the imaging volume 17. The magnet assembly 1 is "open" as the object to be imaged can be moved between the pole assemblies 2, 3 to be positioned at the imaging volume 17.

In this embodiment, each of the first and second pole assemblies 2, 3 comprises both a cylindrical permanent magnet piece 6 (7) and a substantially cylindrical ferromagnetic piece 8 (9). The permanent magnet piece 6 (7) and substantially cylindrical ferromagnetic piece 8 (9) are arranged such that the ferromagnetic piece 8 (9) is positioned between the imaging volume 17 and the permanent magnet piece 6 (7). Inward-facing surfaces, or "pole faces" 4, 5 are adjacent to the space between the first and second pole assemblies 2 and 3. As will be described in further detail herein, each of the first and second ferromagnetic pole assemblies 2, 3 produce a variety of magnetic field strengths across their inward-facing surfaces 4, 5 to produce an acceptably homogeneous magnetic field in the imaging volume. In this embodiment, an acceptably homogeneous magnetic field is one that comprises about 10 ppm, or less, of magnetic field inhomogeneity. This level of inhomogeneity is considered acceptable for use in Magnetic Resonance Imaging (MRI) devices such as those that base imaging on radio frequency signals emitted by protons and detected by a detector 50 within the imaging volume 17 when re-aligning with the substantially homogeneous magnetic field after perturbation.

The ferromagnetic pieces 8, 9 are referred to as "substantially" cylindrical as opposed to strictly cylindrical because while the ferromagnetic pieces 8, 9 are circular when viewed from above (or below) in FIG. 1, respective inward-facing, or "opposing" surfaces or pole faces 4, 5 are not strictly planar in this embodiment. Rather, each ferromagnetic piece 8, 9 is shaped to have a variety of thicknesses of magnetic material (when viewed cross-sectionally) thereby to produce the variety of magnetic field strengths across inward-facing surfaces 4 and 5.

In this embodiment, the magnet assembly 1 also includes a yoke structure 10 with first and second yoke plates 11 and 12 connected with four columns 13-16. The first pole assembly 2 is connected to the inward-facing surface of the first yoke plate 11 which is closest to the second yoke plate 12. Similarly, the second pole assembly 3 is connected to the inward-facing surface of the second yoke plate 12.

As will be understood, in certain magnet applications, such as MRI, a high overall magnetic field strength is required in the imaging volume 17. In this embodiment, to achieve this high magnetic field strength permanent magnet pieces 6 and 7 are formed of a Neodymium-Iron-Boron compound. In an alternative embodiment, another material or materials that are permanently magnetized and have a high maximum energy product may be employed. Furthermore, ferromagnetic pieces 8, 9 and the yoke structure 10 are each formed of iron-bearing material such as steel. As has been described above, it is advantageous particularly for MRI applications to have excellent magnetic field homogeneity in the imaging volume. However, in prior known magnet assemblies, particularly those having planar pole faces, the magnetic field produced by the magnet assembly has generally a poor level of homogeneity. Furthermore, in prior known magnet assemblies, due to the non-axisymmetric shape of the entire magnet assembly and in particular due to the non-axisymmetric shape of the yoke structure, magnetic field inhomogeneities in the imaging volume are accordingly both axisymmetric and non-axisymmetric. As a result, any volume of space that contains an acceptably homogenous magnetic field (i.e. suitable for imaging) in such prior known magnet assemblies is very small compared to the overall size of the magnet assembly, requiring very large magnets to achieve a sufficiently-sized imaging volume.

Figure 8:
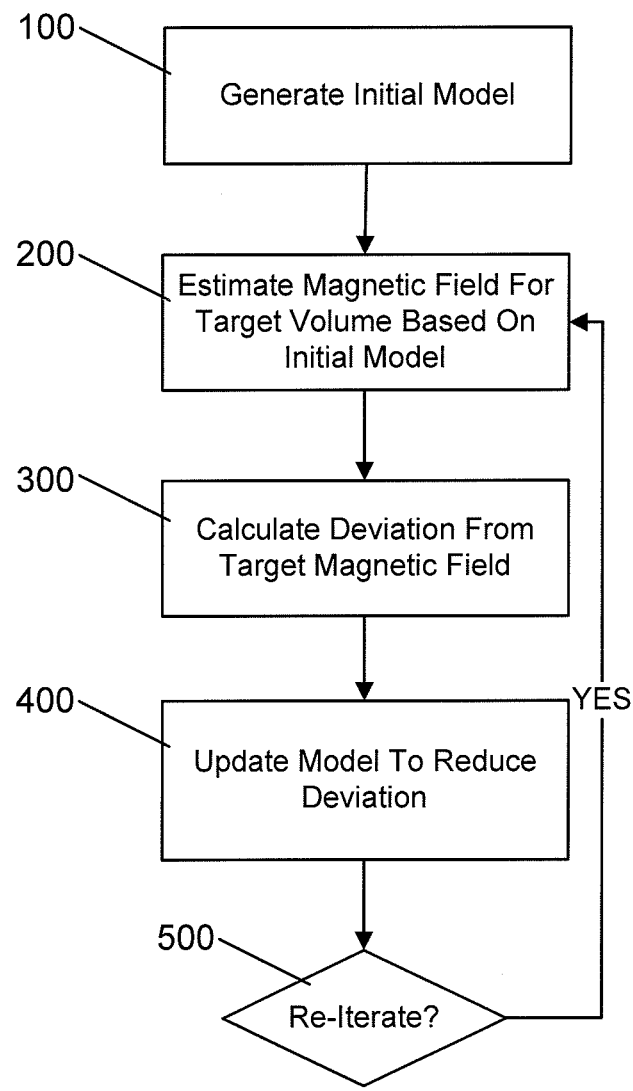
FIG. 8 is a flowchart showing steps for defining a magnetic field for an imaging volume according to an embodiment.

Described herein with reference to FIG. 8 is a method for defining a magnetic field for an imaging volume. During the method, an initial model of a magnet assembly 1 is generated (step 100), and a magnetic field for the imaging volume is determined based on the model (step 200). A deviation between the magnetic field and a target magnetic field for the imaging volume is calculated (step 300), and the model is updated to reduce the deviation by modifying the magnet assembly 1 to produce a variety of magnetic field strengths that, in combination, produce substantially the target magnetic field in the imaging volume (step 400).

If after the updating at step 400 it is determined at that re-iteration is required (step 500), the estimating, calculating and updating steps are performed again.

In this embodiment, the target magnetic field is a homogeneous magnetic field, such that producing substantially the target magnetic field in the imaging volume produces a substantially homogeneous magnetic field in the imaging volume.

Figure 9:
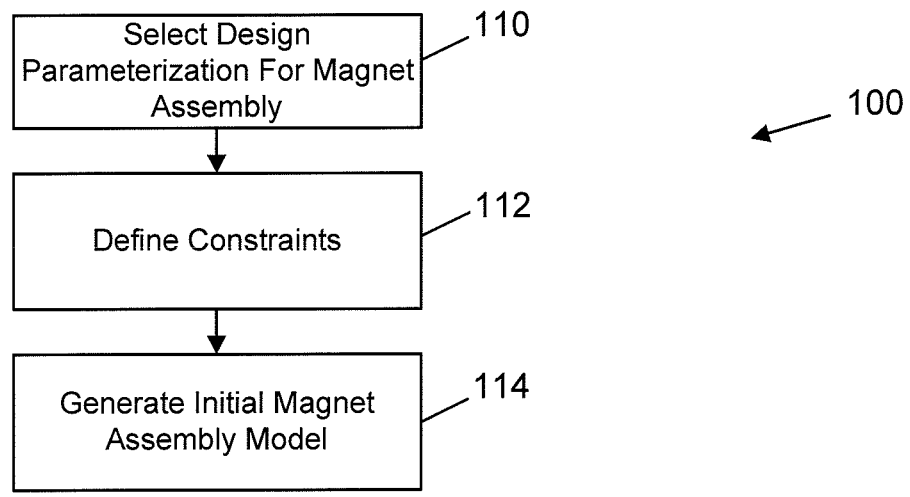
FIG. 9 is a flowchart better illustrating the steps for generating an initial model of a magnet assembly as shown in FIG. 8.
Figure 10:
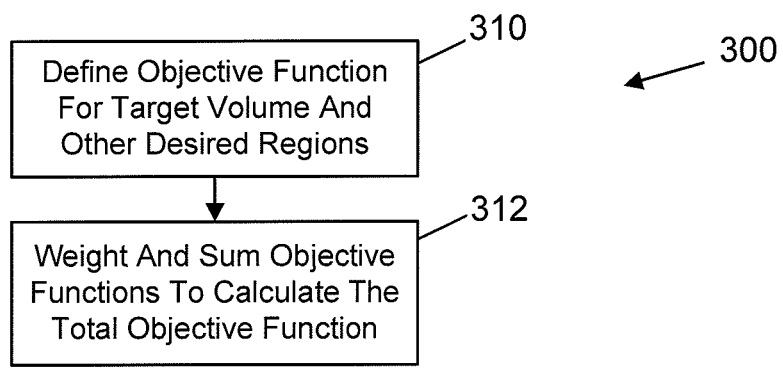
FIG. 10 is a flowchart better illustrating the steps for calculating deviation from a target magnetic field in the form of an objective function as shown in FIG. 8.

FIG. 9 shows in further detail the steps for generating an initial model of the magnet assembly 1, as shown in step 100, above. First, a design parameterization for the magnet assembly 1 that defines parameters representing the shape, dimensions and materials of the magnets and of the magnet assembly 1 is selected (step 110).

Constraints are then defined (step 112) such that the parameters are given initial values and designated as either variable or invariable. The initial values of the design parameters may be selected or predefined in any fashion, including empirically, arbitrarily, or randomly, provided they satisfy the specified constraints. For example, in this embodiment, the materials of the magnet assembly 1 are defined initially as representing the magnetic properties of steel and Neodymium-Iron-Boron compound as described above but designated as invariable such that during the updating of the model the materials may not be varied. On the other hand, in this embodiment the parameters representing the surface geometry of the inward-facing surfaces of the magnets are defined initially as representing planar or "flat" inward-facing surfaces but are designated as variable such that they may be modified to optimize their shape during the updating to produce non-planar inward-facing surfaces as shown in FIG. 1.

With the parameterization, parameter initial values and constraints having been defined thereby to generate the initial model of the magnet assembly (step 114), the magnetic field produced by the initial magnet assembly, and particularly for the imaging volume of interest, is then estimated using a simulation technique employing the finite element method (FEM) or a boundary element method (BEM) (step 300)

With the magnetic field having been estimated, the deviation between the target magnetic field and the magnetic field produced by the magnet assembly as represented by the initial model is then calculated. The deviation to be reduced and preferably minimized is defined as an objective function $\Psi$ (step 310), which can be explicitly or implicitly determined by the set of design parameters. In this embodiment, the objective function $\Psi$ contains at least one term $\Psi_i$ (labelled with the index i=1, 2, . . . ) for each of the regions in which the magnetic field is to be optimized. Thus, at least one term is present, $\Psi_1$, which in this embodiment is a calculation of the deviation of the actual magnetic field from that of a perfectly homogenous magnetic field over the imaging volume 17, as shown in Equation (1) below:

$$\Psi_1 = \int_\Omega (B(r) - B_0)^2 \, d\Omega \qquad (1)$$

where:

B(r) is the magnetic field strength at the location r; and $B_0$ is the desired magnetic field strength.

In this embodiment, the location of the desired magnetic field strength $B_0$ is the point of isocenter of the magnet assembly, or at the center point of the imaging volume 17. In this embodiment, both of these points coincide. The integral in Equation (1) is evaluated over the imaging volume 17, denoted mathematically as $\Omega$. The objective function $\Psi$ contains at least one term for each of the regions in which the magnetic field is to be defined. In this embodiment, at least one term of the objective function $\Psi$ is a measure of the deviation of the actual magnetic field from that of a perfectly homogenous magnetic field, calculated over the imaging volume. However, if it is desired that other regions are also to be optimized, each region has an associated term that is similarly a measure of the deviation of the actual magnetic field from that which is desired in that region, calculated over the region's associated volume. In such a case, the other regions, denoted as $\Omega_i$, require deviation reduction and the ith term $\Psi_i$ of the objective function $\Psi$ is calculated as shown in Equation (2), below:

$$\Psi_i = \int_{\Omega_i} (B(r) - B_i(r))^2 \, d\Omega_i \qquad (2)$$

where:

B(r) is the magnetic field at the location r; and $B_i(r)$ is the desired magnetic field at the location r.

In this case, the preferred total objective function $\Psi$ representing the deviation of the magnetic field estimated to be produced by the magnet assembly 1 from the target magnetic field is calculated simply as a weighted sum of the individual terms (step 312), as shown in Equation (3) below:

$$\Psi = \sum_i w_i \Psi_i \qquad (3)$$

where:

$w_i$ is the user-defined weight for the ith term $\Psi_i$.

The weights $w_i$ serve to scale the individual terms $\Psi_i$ in the sum according to their importance as determined by the user. For example, the imaging volume 17 center point may be accorded a higher weight than a point coinciding with another object or device (such as a detector 50 or a linear accelerator at some position proximate the magnet assembly 1) in order to favour imaging volume homogeneity over interference mitigation.

It will be understood that alternative definitions of the objective function and its individual terms could be used in order to yield reasonable designs satisfying the objects of the present invention. For example, the objective function could include an evaluation of the integrals over the boundaries of the regions denoted Ω and Ω$_i$ above, rather than over the regions themselves.

With the objective function having been defined based on the set of input parameters (and therefore being dependent upon the parameters), a subset of N of the design parameters that are designated as variables are updated to reduce the total objective function Ψ. These N variables to be updated describe the geometry to be optimized. At the kth iteration of the optimization process, the design vector $z_k$ is defined to be the vector whose elements are the individual variable parameters, as shown in Equation (4) below:

$$z_k = [z_{k1} z_{k2} \ldots z_{kN}] \quad (4)$$

where:

$z_{kj}$ is the jth variable parameter at the kth iteration, for $j=1, \ldots, N$.

Figure 2:
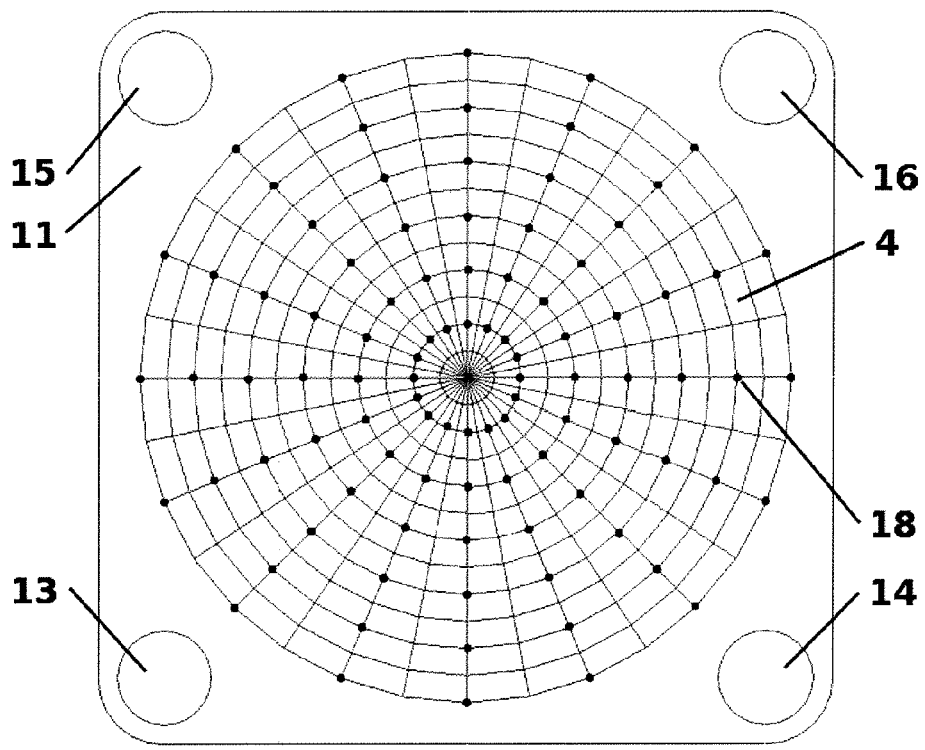
FIG. 2 is a cross-sectional view of an open compact magnet assembly of the present invention, including a direct view of the pole assembly surface and the distribution of variable design parameters representing locations on the pole assembly surface.
Figure 3:
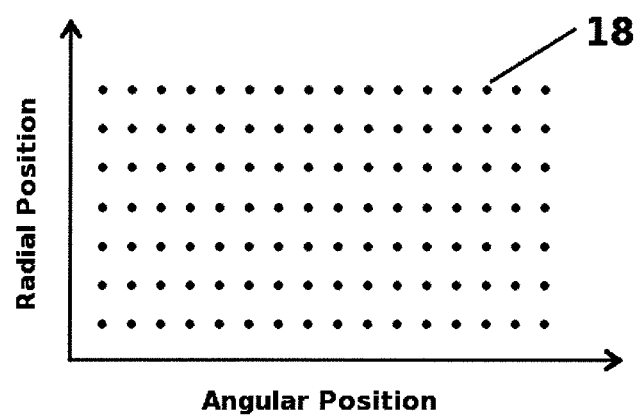
FIG. 3 is a graph plotting the radial position versus the angular position of the variable design parameter distribution of locations on the pole assembly surface.

In this embodiment, the inward-facing surfaces (pole faces 4 and 5) are to be contoured in order to reduce the deviation thereby to produce the target magnetic field. The variables used represent respective axial locations of a collection of points 18 on the pole faces 4 and 5, as shown in FIG. 2. In FIG. 2, the locations are measured with respect to a first axis extending generally from the center of the first pole assembly 2 to the center of the second, opposing pole assembly 3. The points are arranged such that a plot of their radial position versus their angular position, both measured relative to the first axis, forms a two dimensional grid as shown in FIG. 3. The actual pole faces 4 and 5 are then described by a linear interpolation between the set of the variable parameters that are located on each of the pole faces 4 and 5. As would be understood, the constraints that these variable parameters are to satisfy are provided in order to ensure a physically reasonable design. As such, preferably such constraints include a range of permissible values of the axial position of the points on the pole faces 4 and 5, thus enforcing a minimum axial width of the pole assemblies 2 and 3, as well as a minimum separation between the two opposing pole assemblies 2 and 3.

Advantageously, the pole assemblies 2 and 3 resulting from the above-described parameterization are not necessarily restricted to be axisymmetric. As such, the beneficial reduction of both axisymmetric and non-axisymmetric magnetic field inhomogenieties in the imaging volume 17 is provided, and beneficial tailoring of the magnetic field produced in any region within or proximate the magnet assembly 1 is permitted to accommodate other objects and/or devices that may interfere with the magnetic field or be interfered with by it.

The design parameterization described here is presented for the purpose of illustration, as there are many other variations or choices of what parameters are designated as variable and how those parameters relate to the actual geometries they are meant to describe. For example, the collection of points described above may not necessarily actually lie on the surface of the pole faces 4 and 5, but may rather be weighted control points that are used for some other method of interpolation which defines the actual pole faces 4 and 5. The number and geometric distribution of the control points may also be chosen in some other way, based on the requirements of the designer. Furthermore, additional design parameters could be designated as variable, such as the location, orientation, or other various dimensions of the pole assemblies 2 and 3, as well as particular material properties, such as the magnetization distribution of the permanent magnet pieces 6 and 7.

During the updating (step 400), at each iteration a nonlinear mathematical optimization algorithm is employed in order to adjust each of the variable design parameters to reduce the value of the objective function Ψ thereby to reduce the deviation. It has been found that the objective function Ψ is highly nonlinear with respect to the design parameters. As such, a robust nonlinear optimization algorithm is employed in order to achieve convergence within an appropriately prescribed tolerance on a local minimum of the objective function Ψ within a reasonable number of iterations. In this embodiment, the nonlinear optimization algorithm employed is the method of steepest descent. In general, the design vector at the (k+1)th iteration is obtained from the design vector at the kth iteration, as shown in Equation (5) below:

$$z_{k+1} = z_k + \alpha_k d_k \quad (5)$$

where:

$\alpha_k$ is the scalar step size in the search direction vector $d_k$.

The step size $\alpha_k$ scales the amount by which the design vector is updated in the search direction at the kth iteration. Step size $\alpha_k$ is determined using an inexact line search algorithm. According to the steepest descent method, the search direction vector $d_k$ is defined, as shown in Equation (6) below:

$$d_k = -\nabla \Psi_k \quad (6)$$

where:

$\nabla$ is the gradient operator; and $\nabla \Psi_k$ is the gradient vector of the objective function with respect to the variable design parameters, evaluated at the kth iteration.

The jth element of $\nabla \Psi_k$ is calculated, as shown in Equation (7) below:

$$(\nabla \Psi_k)_j = \frac{\partial \Psi_k(z_{kj})}{\partial z_{kj}} \quad (7)$$

While the first derivatives in Equation (7) required by the method of steepest descent may not be determined exactly, they may be approximated. While several methods of approximating the first derivatives may be employed, one of the simplest methods is to calculate each first derivative based on a finite difference approximation. The finite difference approximation includes calculating a difference between the objective function Ψ for the design where a single variable parameter $z_{kj}$ is perturbed a small finite amount δz from its normal value at that particular iteration, and the objective function Ψ for the unperturbed design at that iteration, as shown in Equation (8) below:

$$\frac{\partial \Psi_k(z_{kj})}{\partial z_{kj}} \approx \frac{\Psi_k(z_{kj} + \delta z) - \Psi_k(z_{kj})}{\delta z} \quad (8)$$

Figure 4:
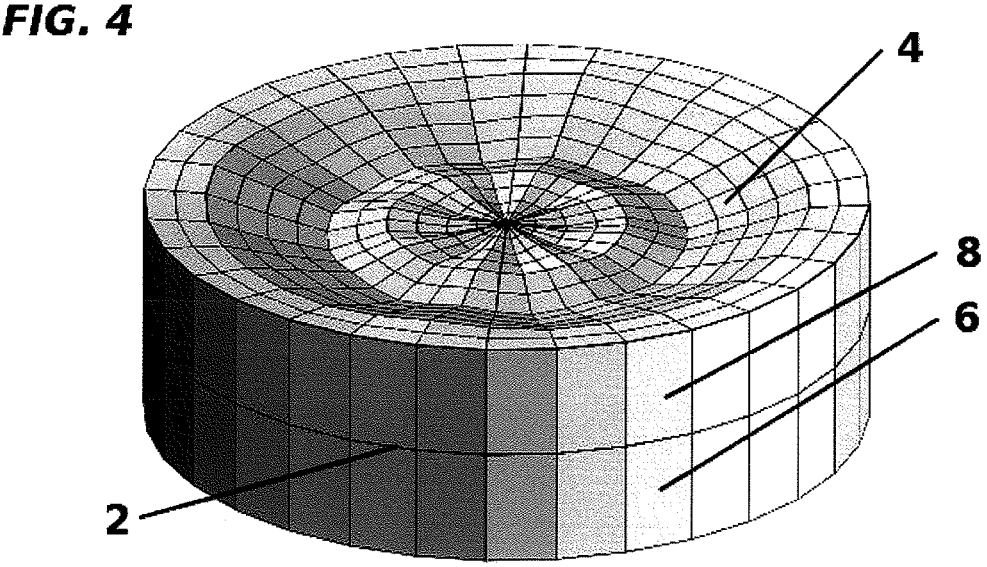
FIG. 4 is a perspective view of a contoured non-axisymmetric pole assembly in isolation according to an embodiment.

FIG. 4 shows in isolation the pole assembly 2 of FIG. 1. A substantially cylindrical shape with a completely flat/planar surface was empirically chosen for the initial model as part of the magnet assembly. After execution of the optimization method described above, the model was updated such that the value for the single-term objective function Ψ for the magnet assembly 1 was locally minimized and a large, homogenous magnetic field in the imaging volume 17 was obtained. More particularly, the variable parameters representing locations on the inward-facing surface 4 of ferromagnetic pole piece 8 of pole assembly 2 were modified during the updating from the initial planar configuration to represent a contoured inward-facing surface 4. As can be seen, the contouring provides varying amounts of magnetic material across the volume of the ferromagnetic pole piece 8.

Due to the non-axisymmetric yoke structure 10 (see FIG. 1), the resulting ferromagnetic pole piece 8 was non-axisymmetric. Due to the variations in thicknesses of magnetic material across its volume, pole assembly 2 in conjunction with similarly-formed pole assembly 3 produces a variety of magnetic field strengths across its inward-facing surface 4 that combine to produce a substantially homogeneous magnetic field in the imaging volume 17.

The principles set out in the above-described example may be applied to achieve additional objectives, such as for updating the model to incorporate, in addition to the magnet assembly, one or more objects and/or devices capable of disturbing the magnetic field in the imaging volume in a manner that would cause the magnetic field in the imaging volume to be unacceptably inhomogeneous. For example, such objects may include physical barriers in a treatment room, one or more devices such as a linear accelerator, an imaging detector or other object, and so forth. In such a case, the estimating, calculating and updating would be performed based on this updated model. One or more of such devices may also be themselves capable of being disturbed by the magnetic field in the imaging volume in a manner that would cause the one or more devices to operate unacceptably. The method may further include modifying the target magnetic field based on the updated model to, for example, reduce interference of the magnetic field with the one or more devices. Modifications may include modifying the shape of the imaging volume to accommodate proximate devices, or modifying the acceptability threshold of inhomogeneity to accommodate the proximate devices. Such devices may be inserted into the space defined by the magnets, and/or positioned within a hole vacated in one or more of the magnets.

According to an embodiment, the method for defining a magnetic field to incorporate additional objects and/or devices or to incorporate a hole vacated in one or both of the magnets is performed in multiple sequential stages. In each stage, one or more of the described modifications are incorporated into the design of the magnet assembly obtained from the optimization at the previous stage. Any new associated constraints and additional terms desired in the objective function associated with the newly incorporated modifications are also included and the deviation-reduction method is executed again, resulting in a magnet assembly design for that stage. Multiple stages are executed until all desired modifications have been incorporated into the computer model simulation and a final design is obtained. The modifications may be placed in any particular order within the overall design optimization scheme, and the design parameters designated as variables need not remain the same between different stages.

Figure 5:
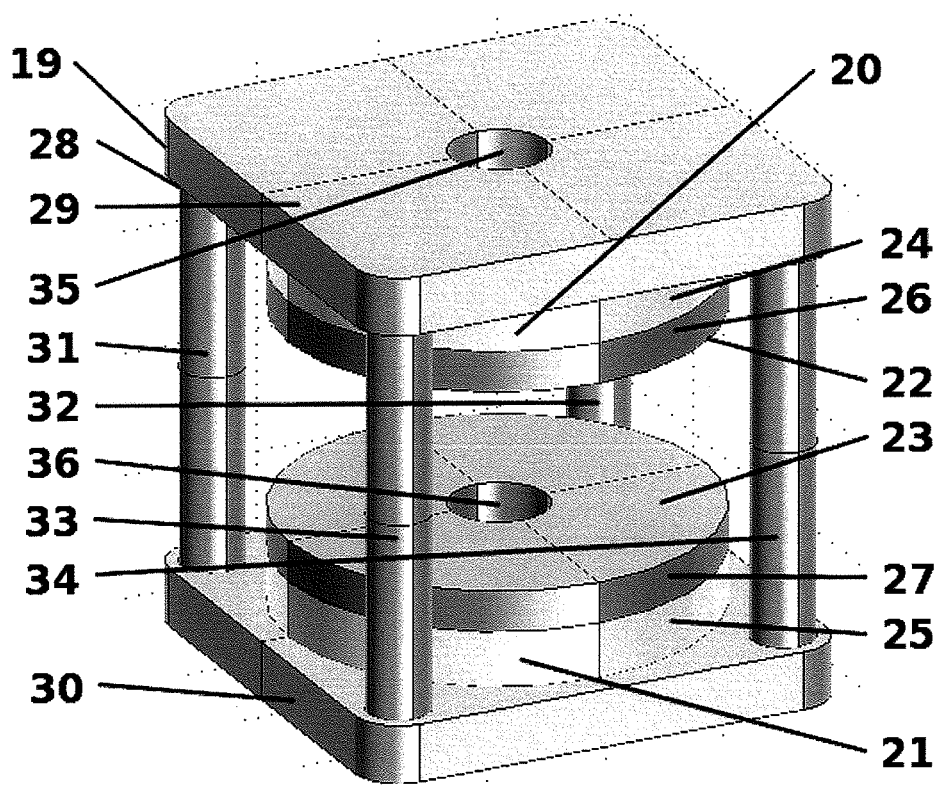
FIG. 5 is a perspective view of an alternative open compact magnet assembly, having in particular two large holes vacated through the entire magnet assembly.
Figure 6:
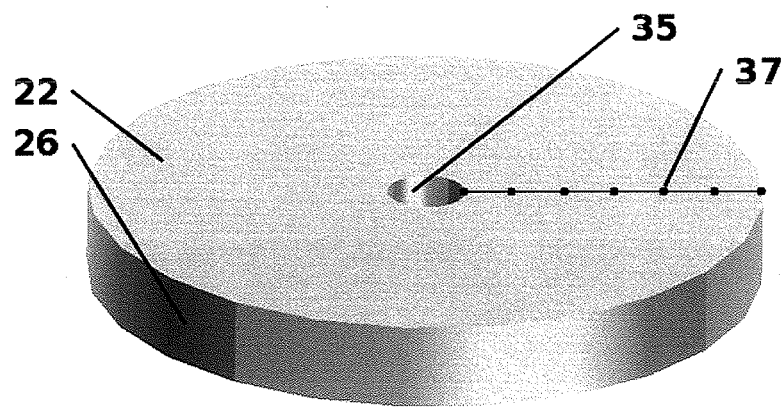
FIG. 6 is a perspective view of a planar-faced ferromagnetic pole piece in an initial model of a magnet assembly, having a large hole vacated therethrough, along with the distribution of surface locations represented by variable design parameters.
Figure 7:
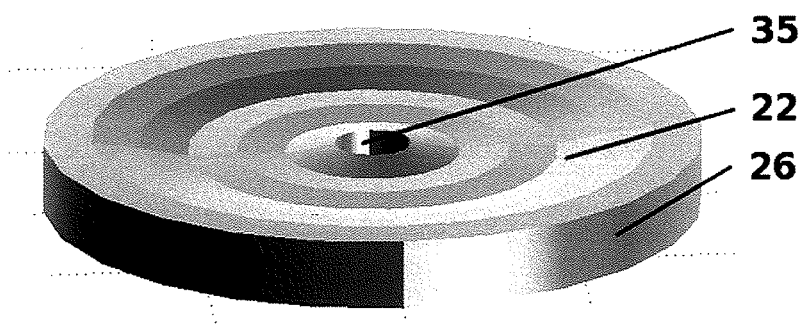
FIG. 7 is a perspective view of an axisymmetrically contoured ferromagnetic pole piece resulting from application of the method to the magnet assembly incorporating the pole piece of FIG. 6.

An embodiment of a magnet assembly 19 having two large holes 35 and 36 vacated through the entire magnet assembly 19 is shown in FIGS. 5 to 7. More particularly, the first and second holes 35 and 36 are vacated from the first and second pole assemblies 20 and 21, as well as the first and second yoke plates 29 and 30 of the yoke structure 28, respectively. For defining the magnetic field, a different parameterization than that of the previously-described embodiment is employed, wherein an axisymmetric pole assembly is achieved by selecting the design variables to be the axial position of a collection of points 37 that lie along a radial line of the pole assembly surfaces 22 and 23. This is shown particularly in FIG. 6. The pole assembly surface 22 is then formed by linearly interpolating the axial position between adjacent points 37 and then constraining all points on the surface 22 that are an equal radial distance from the center of the pole assembly to have an equal axial position. In other words, the points 37 designate the height of a series of annular concentric frustoconical segments on the pole assembly surface 22. As would be understood, the design parameterization in this embodiment may be substituted by other variations or choices as to which parameters are designated as variable, and how such parameters relate to the actual surface geometry.

FIG. 7 shows an embodiment of a ferromagnetic pole piece 26, having been modified during the updating as described above from the planar surface of FIG. 6 to the non-planar/undulating surface shown. More particularly, a substantially cylindrical shape with a completely flat surface was empirically chosen as the initial design for the pole piece and the optimization method was executed to update the design such that the value for the single-term objective function Ψ for the magnet assembly 19 was locally minimized to obtain a large, homogenous magnetic field in a spherical imaging volume at the magnet assembly isocenter (not shown in the Figures).

The method described herein for defining a magnetic field for an imaging volume, and the initial and updated models may be embodied in one or more software applications comprising computer executable instructions executed by the server and other devices. The software application(s) may comprise program modules including routines, programs, object components, data structures etc. and may be embodied as computer readable program code stored on a computer readable medium. The computer readable medium is any data storage device that can store data, which can thereafter be read by a computing device. Examples of computer readable media include for example read-only memory, random-access memory, CD-ROMs, magnetic tape and optical data storage devices. The computer readable program code can also be distributed over a network including coupled computer systems so that the computer readable program code is stored and executed in a distributed fashion.

It will be understood that alternative embodiments can be conceived of based on the teachings herein. For example, the first and second pole assemblies described above may be substituted with, or accompanied by, a coil magnet configuration. In such an embodiment, the optimization parameters varied in the design process to produce the variety of magnetic field strengths could include any combination of the parameters already described herein, as well numerous parameters related to coil magnet design, such as the number of coil turns, the coil current, coil wire gauge, coil shape, and coil location.

While the estimating, calculating and updating during the above-described method is iteratively performed a threshold number of times, alternatives are possible. For example, the estimating, calculating and updating may be performed iteratively until a magnitude of the deviation represented by the objective function Ψ falls below a threshold level, or alternatively until the magnitude of the deviation represented by the objective function Ψ fails to change by more than a threshold amount between successive iterations.

While the method of steepest descent as described above is used to perform nonlinear optimization, other mathematical nonlinear optimization algorithms available in the literature may alternatively be used. Such alternative algorithms include simplex methods, conjugate gradient methods, or a combination of the steepest descent, simplex and conjugate gradient methods.

While the finite difference approximation has been described above for estimating the first derivatives of Equation (7), the first derivatives can alternatively be approximated using more complicated techniques and approximation formulas known to those skilled in the art. One such technique is known as design sensitivity analysis.

While the above has been described primarily for defining a target magnetic field for an imaging volume, where in particular embodiments the target magnetic field is a substantially homogeneous magnetic field, other applications are contemplated. For example, the target magnetic field for the imaging volume may not be a substantially homogeneous magnetic field, but rather be a nonhomogeneous magnetic field with a specific gradient having a slope and direction that is predefined for a particular application. More generally, applications are contemplated in which the target magnetic field is for use not with imaging, but for other functions. One such function is that of directing particles such as electrons, protons or photons emitted by a radiation therapy device. For example, it may be desired to define a magnetic field for a target volume for directing/guiding/changing the path of an electron, photon, or proton beam (for proton therapy) in accordance with its energy such as is done currently with the use of bending magnets. Various applications can be served by the method described above in which the two or more magnets of magnet assembly are identical or mirror images of one another, or in which the two or more magnets of the magnet assembly are dissimilar for achieving desired results, such as bending as described above. As such, while in the initial model the magnets may be alike in that they are identical or mirror images of one another, as well as each having planar inward-facing surfaces, in the updated model in accordance with constraints and requirements, the two magnets may result as dissimilar in the sense that they are not exactly alike, in order to achieve bending or a gradient for imaging, etc. In fact, depending upon the constraints and requirements, the two magnets may be shaped and dimensioned quite different from one another in the updated model so as to achieve the desired results.

Although embodiments have been described, those of skill in the art will appreciate that variations and modifications may be made without departing from the purpose and scope thereof as defined by the appended claims.

What is claimed is:

1. A method of defining a target magnetic field for a target volume in a Magnetic Resonance Imaging (MRI) machine, the method comprising:

generating an initial model comprising:
a magnet assembly comprising a first magnet and a second magnet maintained in a fixed spaced relationship by a yoke assembly, the magnet assembly having an axis extending generally from a center of the first magnet to a center of the second magnet, the first and second magnets being axisymmetrically shaped; and
one or more fixed objects, including the yoke assembly, capable of disturbing the magnetic field in the target volume in a non-axisymmetric manner that would cause the magnetic field in the target volume to be unacceptably inhomogeneous for imaging;

estimating a magnetic field for the target volume based on the model;
calculating deviation between the estimated magnetic field and the target magnetic field for the target volume; and
updating the model to reduce the deviation by non-axisymmetrically modifying one or more parameters representing one or both of the first and second magnets to produce a variety of magnetic field strengths that, in combination, produce substantially the target magnetic field in the imaging volume.

2. The method of claim 1, wherein each of the magnets is a permanent magnet and has an opposing inward-facing surface, wherein the one or more parameters represent a surface geometry of one or both of the inward-facing surfaces.

3. The method of claim 2, wherein variable parameters representing the surface geometry of one or both of the inward-facing surfaces comprise positions along a longitudinal axis of the magnet assembly of respective points on the inward-facing surfaces.

4. The method of claim 2, wherein in the initial model the parameters specify that the inward-facing surfaces of the magnets are planar, and during the modifying the parameters are modified to specify that at least one of the inward-facing surfaces of the magnets is not planar.

5. The method of claim 1, wherein the parameters further represent at least one of: magnet shape, magnet dimensions, magnet material, and magnet assembly sizes.

6. The method of claim 5, wherein the one or more parameters represent at least the magnet shape and magnet dimensions.

7. The method of claim 5, wherein the method is restricted to modifying the magnet assembly size within a range of permissible magnet assembly sizes.

8. The method of claim 1, wherein the target magnetic field is an acceptably homogeneous magnetic field for imaging, and the method further comprises:
generating an updated model incorporating, in addition to the magnet assembly, one or more devices capable of disturbing the magnetic field in the imaging volume in a manner that would cause the one or more devices to operate unacceptably;
modifying the target magnetic field based on the updated model to reduce interference of the magnetic field with the one or more devices; and
performing the estimating, calculating and updating based on the updated model.

9. The method of claim 8, wherein modifying the imaging volume comprises modifying the shape of the imaging volume.

10. The method of claim 8, wherein modifying the target magnetic field comprises modifying an acceptability threshold of inhomogeneity.

11. The method of claim 1, wherein the estimating, calculating and updating are performed iteratively either a threshold number of times, and/or iteratively until the magnitude of the deviation falls below a threshold level, and/or iteratively until the magnitude of the deviation fails to change by more than a threshold amount between successive iterations.

12. The method of claim 1, wherein the at least two magnets in the initial model are alike and the at least two magnets in the updated model are alike.

13. The method of claim 1, wherein the at least two magnets in the initial model are alike and the at least two magnets in the updated model are dissimilar.

14. A non-transitory computer readable medium embodying a computer program for defining a target magnetic field for a target volume in a Magnetic Resonance Imaging (MRI) machine, the computer program comprising:

computer program code generating an initial model comprising:
- a magnet assembly comprising a first axisymmetrically shaped magnet and a second axisymetrically shaped magnet maintained in a fixed spaced relationship by a yoke assembly, the magnet assembly having an axis extending generally from a center of the first magnet to a center of the second magnet; and
- one or more fixed objects, including the yoke assembly, capable of disturbing the magnetic field in a non-axisymmetric manner that would cause the magnetic field in the target volume to be unacceptably inhomogeneous for imaging;

computer program code estimating a magnetic field for the target volume based on the model;

computer program code calculating deviation between the estimated magnetic field and the target magnetic field for the target volume; and computer program code updating the model to reduce the deviation by non-axisymmetrically modifying one or more parameters representing the magnet assembly to produce a variety of magnetic field strengths across one or both of the first or second magnets that, in combination, produce substantially the target magnetic field in the target volume.

* * * * *